United States Patent [19]

Piquard

[11] 4,169,463

[45] Oct. 2, 1979

[54] DEVICE FOR RHEOPLETHYSMOGRAPHY BY OCCLUSION

[75] Inventor: Jean-François Piquard, Vizille, France

[73] Assignee: Commissariat a l'Energie Atomique, Paris, France

[21] Appl. No.: 803,776

[22] Filed: Jun. 6, 1977

[30] Foreign Application Priority Data

Jun. 16, 1976 [FR] France .................................. 76 18224

[51] Int. Cl.$^2$ .............................................. A61B 5/02
[52] U.S. Cl. .................................................. 128/693
[58] Field of Search ................ 128/25, 2.05 A, 2.05 P, 128/2.05 V, 2.1 Z

[56] References Cited

U.S. PATENT DOCUMENTS

| 2,827,040 | 3/1958 | Gilford | 128/2.05 A |
| 3,847,142 | 11/1974 | Williams, Jr. et al. | 128/2.05 V |
| 4,059,169 | 11/1977 | Hagen | 128/2.05 V |

*Primary Examiner*—William E. Kamm
*Attorney, Agent, or Firm*—Pearne, Gordon, Sessions, McCoy & Granger

[57] ABSTRACT

The device for studying vascular behavior particularly in a lower limb of a patient comprises pressure applying means for causing occlusion of the limb under study, means for controlling the characteristics of progressive variation in the pressure applied by the pressure-applying means as a function of time during occlusion of the limb under study, a plethysmograph for delivering signals which are representative of an electrical impedance related to the limb under study and of variations in such electrical impedance, and means for determining, from coefficients of standardization which are characteristic of the healthy vascular operation of a normal limb of the same type as the limb under study and from the signals, indices which are representative of the vascular behavior of the limb under study.

14 Claims, 7 Drawing Figures

DEVICE FOR RHEOPLETHYSMOGRAPHY BY OCCLUSION

This invention relates to a device for measurement, recording and interpretation of rheoplethysmographic signals and permits diagnosis of thromboembolic disorders or the like as a result of better knowledge of the vascular state of, for example, the lower limbs of a patient.

A method which consists in making use of electrodes which are in contact with the skin for the purpose of applying an electric current of low intensity and low frequency to a limb to be examined and in collecting a potential between two other intercalary electrodes is already well known. The potential collected between said intercalary electrodes is in fact proportional to a bioelectric impedance resulting from the connection of three impedances in parallel, namely an extracellular, intracellular and blood impedance respectively. The signals, or plethysmograms, obtained under these conditions are representative of the arterial behavior of the limb under examination and are presented in the form of a pressure wave, the periodicity of which is that of the heart. Another type of variation in the impedance mentioned above (or plethysmogram) which is essentially representative of the slow variations in volume of the vascular territory under inspection can produce useful information on the vascular vasomotor activity or on the modifications in arterial or venous haemodynamic pressure. However, the blood flow rate also has an influence on this variation of impedance, which generally makes it difficult to ensure correct interpretation of plethysmogram measurements.

Another method which is also known is that of rheoplethysmography by occlusion. This method is intended to provide information on the state of the venous system in the limb under examination and makes it necessary to apply to the limb a disturbance usually consisting of an occlusion of the veins for ensuring the return of the blood to the heart. In accordance with the usual technique, use is made of a pneumatic limb-encircling collar which establishes an occlusion pressure on the limb, the collar being inflated by a conventional compressor in accordance with a given law. This occlusion pressure is lower than the minimum arterial pressure itself in order to prevent blood circulation at the inlet of the vascular system of the limb under examination. A measuring transducer, a mercury gage or, preferentially, rheoplethysmography electrodes make it possible to measure the variation in volume of the limb under examination either directly or by determining the resultant variation in impedance which is related to the volume by a known relation.

The instruments which are employed at the present time for the application of rheoplethysmograph by occlusion method are not well adapted to accurate quantitative measurement. In particular, information which is suitable for making a diagnosis cannot be supplied directly by these instruments. Moreover and in accordance with the known method, it is necessary to carry out simultaneous and symmetrical recording on both the lower limbs of the patient, the results obtained being valid only if the mean limb resistances measured are identical. In pathological cases and especially in cases of phlebitis or venous thromboses, the presence of edemas reduces the value of the electrical resistance and consequently impairs the accuracy of measurement of the recorded signal.

The present invention provides a device for rheoplethysmography by occlusion which delivers quantitative signals which are standardized and can consequently be immediately utilized for diagnosis by automatic comparison with reference thresholds which are pre-established by calibration of the device.

Theoretically, it is known that the variation in volume $\Delta v$ of a limb under examination in accordance with the rheoplethysmography by occlusion method, is related to the variation in its impedance $\Delta R$ by the formula:

$$\Delta v = (\Delta R \times \rho \times l^2)/R^2 \tag{1}$$

where
$\rho$ is the resistivity of the blood,
$l$ is the distance between the measuring electrodes associated with the plethysmograph utilized,
$R$ is the mean impedance of the limb as measured between said electrodes.

It has been statistically determined that this variation in volume $\Delta v$ can be considered proportional to the variation in impedance $\Delta R$ in accordance with a formula:

$$\Delta v = K \Delta R / R^n \tag{2}$$

where n has a value within the range of 1 to 1.5 and optimized at 1.3.

The device in accordance with the invention makes it possible to utilize the corrective factor $R^n$ by applying this latter directly to the measurement and the recording of the variation in limb impedance.

It should further be noted that, in order to obtain a perfectly representative quantitative measurement, the measurements taken should be compared automatically with a series of pre-established threshold values as determined by a preliminary statistical study of healthy limbs of a reference population. This makes it possible to determine the limiting values of characteristic indices of vascular behavior and to determine on the basis of the threshold values aforesaid the limits of pathological fields as defined by suitable processing of the values of these different indices.

The device in accordance with the present invention provides a suitable corrective factor as directly applied to the variation in measured limb impedance with the effect of calibration in accordance with a scale resulting from a preliminary healthy population statistical study while making it possible as a result of comparison of characteristic indices with pathological threshold values to carry out a coordinate processing of the different indices which are conducive to a suitable diagnosis.

Finally, the invention provides a device in which the characteristics of the occlusion which is brought about can be varied according to requirements with a view to producing particular sequences of compression and relaxation of the vascular territory to be studied. The device of the present invention is also capable of combining the information resulting from this occlusion with further measurements taken independently of this latter such as the variation in impedance resulting from arterial pressure, venous pressure and oscillations of blood pressure as a function of time, for example.

The present device is adapted in particular to the study of vascular behavior of a lower limb of a patient.

The device includes pressure-applying means for causing occlusion of a lower limb under study, means for controlling the characteristics of progressive variation in the pressure applied by the pressure-applying means as a function of time during occlusion of the limb under study, a plethysmograph for delivering signals which are representative of an electrical impedance related to the limb under study and of the variations in such electrical impedance, and means for determining, from coefficients of standardization which are characteristic of the healthy vascular operation of a normal limb of the same type as the limb under study and said signals, indices which are representative of the vascular behavior of said limb under study.

Further distinctive features of a device, in accordance with the invention, for rheoplethysmography by occlusion will also become apparent from the following description of a number of embodiments which are given by way of example and not in any limiting sense, reference being had to the accompanying drawings, wherein.

Figure 1:
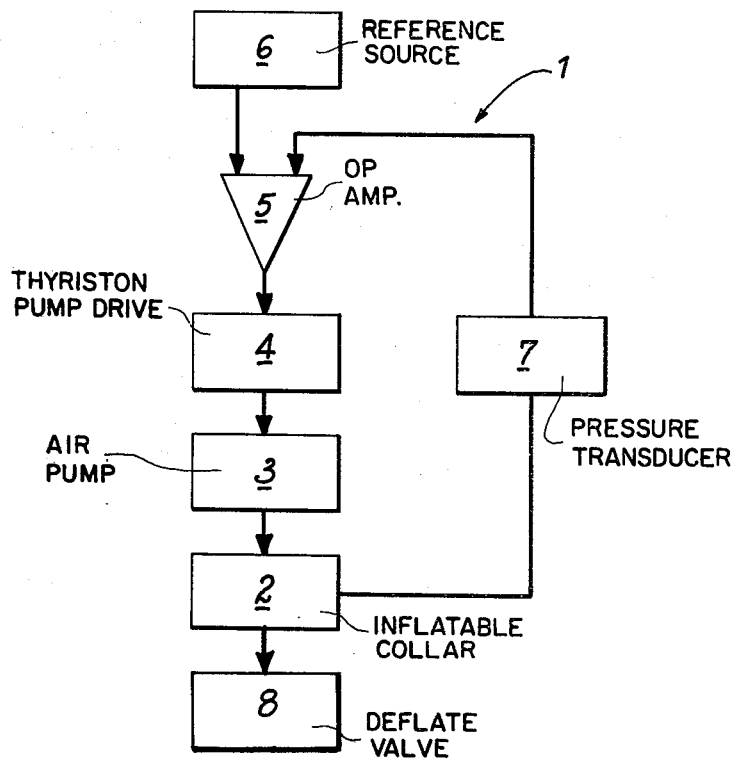
FIG. 1 is a block diagram illustrating the general arrangement of the occlusion circuit for use in the device in accordance with the invention for controlling the characteristics of occlusion in dependence on a predetermined reference value.

In FIG. 1, a control loop 1 is employed for controlling a pneumatic limb encircling collar 2 and for adjusting the pneumatic pressure within this latter on a lower limb under study (not shown). The collar 2 is pressurized by means of a diaphragm air pump 3 or the like which is in turn controlled by a thyristor drive circuit 4 of a known type. The control loop 1 includes a comparison operational amplifier 5. A reference source generator 6 provides a reference signal applied to one of the inputs of said the amplifier 5. The reference signal can consist of a step signal, a ramp signal, a composite signal or a signal having any other waveform such as a sine wave or the like. A voltage delivered by the comparison operational amplifier 5 thus produces a controlling action on the pneumatic collar 2, the pressure of which is measured by means of a conventional miniaturized transducer 7, the output of said transducer being connected as feedback to the second input of the comparison amplifier 5. The characteristics of the diaphragm air pump 3 are advantageously chosen so as to ensure that the pump 3 is capable of inflating the pneumatic collar 2 in less than four seconds in the case of occlusion from a step-function reference signal provided by the reference source generator 6 which produces an instantaneous pressure of the order of 50 mmHg. Evacuation or deflation of the pneumatic garrot at the end of occlusion is carried out by means of collar-deflating, solenoid-actuated exhaust valve 8 which deflates the collar 2 to fully release or partially reduce the occlusion pressure on the limb.

Figure 2:
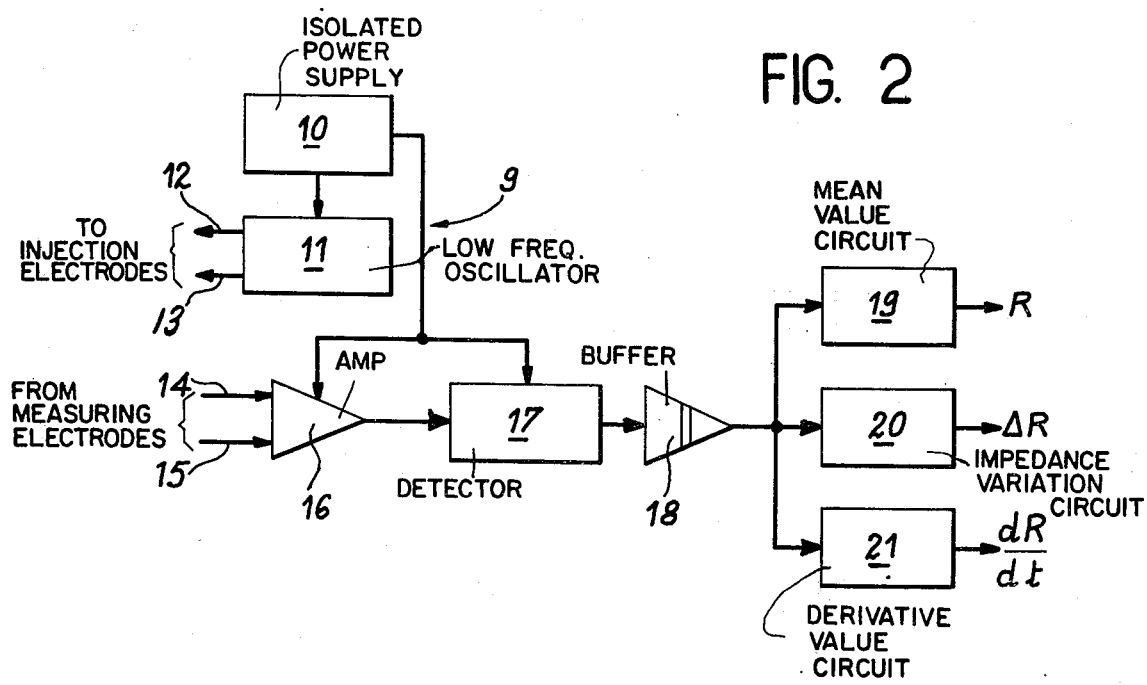
FIG. 2 is a block diagram representing a plethysmograph employed in the construction of a device embodying the present invention.

With reference to FIG. 2, the device in accordance with the present invention includes a fourpole plethysmograph or a known 21 type or impedance plethysmograph for measuring the mean impedance R of the limb under study between two suitable electrodes and for measuring the variations $\Delta R$ in said limb impedance. The plethysmograph generally designated in FIG. 2 by the reference numeral 9 is of a known type and includes in particular an oscillator 11 having a very high output impedance connected to an power supply 10 and delivers at two outputs 12 and 13 respectively an injection current of low intensity which passes through the limb under study. Two other leads 14 and 15 connected to the intercalary measuring electrodes (not shown), preferably mounted on each side of the calf under study are then connected to a measuring amplifier 16 having a very high input impedance, the output of amplifier 16 controls a detecting and filtering device 17. The output of the detector 17 passes through a buffer amplifier 18, the output of which is provided to three circuits 19, 20 and 21. Said circuits 19, 20, 21, of conventional design, supply respectively the mean value of the measured impedance R, the variations $\Delta R$ in said impedance as the variation takes place in the volume of the limb as a result of occlusion and at the time of release or reduction of the occlusion, and the value of the derivative dR/dt, the value of which provides an arterial rheogram.

Figure 3:
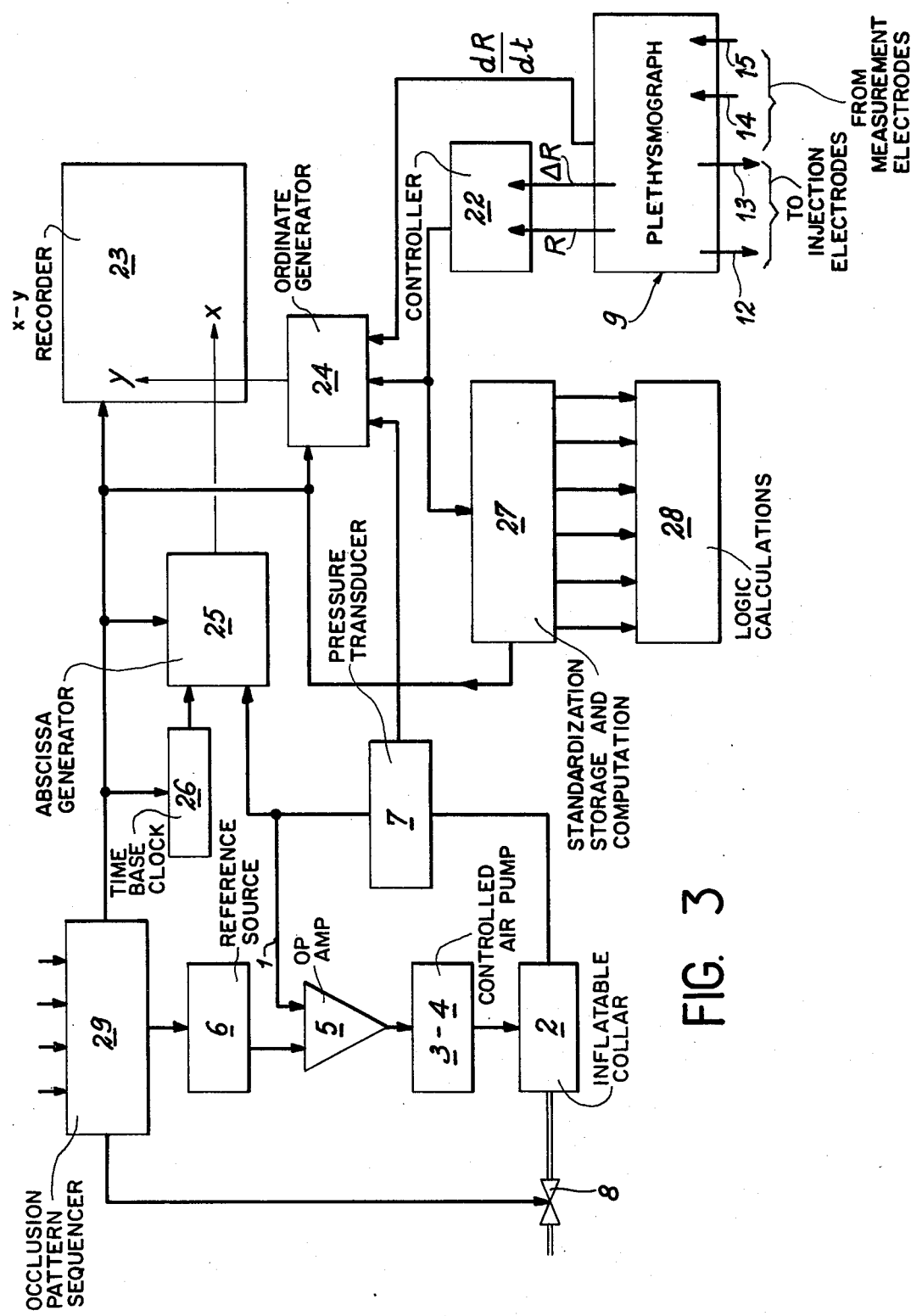
FIG. 3 is a block diagram illustrating the general arrangement of the device in accordance with the invention.

Turning to FIG. 3, there is illustrated a device in accordance with the present invention. The plethysmograph 9 is directly associated with a conventional analog computation module or controller 22 which permits correction by means of the signals derived from the circuits 19 and 20 (FIG. 2) for giving the values of R and of $\Delta R$ while also making it possible to transpose the measurement of said signals to a measurement of variation in volume of the limb in accordance with the earlier discussed formula:

$$\Delta v = (k\, \Delta R / R^n) \qquad (2)$$

By utilizing these volume variation measurements indices can be determined to permit direct control of the results of the test on a visualization recorder 23 or on galvanometers (not shown).

As illustrated in FIG. 3, the device 23 is an X/Y recorder in which the values of abscissae which can depend on the nature of the characteristics of the occlusion, the time or the pressure and the values of ordinates are derived from two circuits 24 and 25 for selection of X and of Y. An abscissa circuit 25 receives a signal derived from a time base clock 26 or a pressure signal derived from the transducer 7. The signals obtained from the analog computation module 22 can be directed to a standardization storage and computation device 27 of any known type. By means of standardization signals provided by the plethysmograph, the device 27 provides measuring indices, such as filling rate index, the index of distensibility at the time of limb filling, the index of evacuation rate, the index of evacuation or of contraction and the evacuation time constant. At the output of the storage device 27, the measuring indices are directed to a logic operator 28 for assisting diagnosis which, as a result of a suitable combination of these indices and statistical comparison with suitable reference values in accordance with pre-established diagrams, will make it possible to define the diagnosis. Finally, by driving the occlusion-controlling unit of the reference-signal generator 6, an occlusion pattern sequencer 29 makes it possible to vary the waveform of said signal so as to correspond to a step, a ramp or any other curve adapted to the particular test which is desired.

In accordance with the invention, the device for rheoplethysmography by occlusion as described in the foregoing operates as follows: in a first step, the inflatable collar 2 is placed downstream of the electrode position on a limb to be examined. Pressure on the limb is established in accordance with a predetermined reference value by means of the diaphragm pump. In all cases, the maximum value of limb pressure is lower than the minimum arterial pressure in order to permit filling of the limb under study with the incident blood-flow.

In a simplified embodiment of the invention which permits the construction of a portable apparatus, the X/Y recorder is replaced by a number of galvanometers corresponding in each case to one index.

Figure 4:
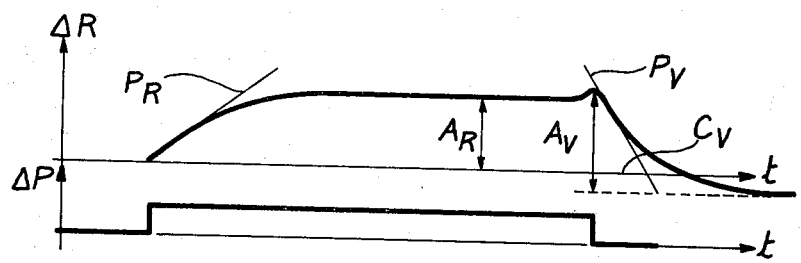
FIGS. 4 and 5 are curves showing the variation in measured impedance as a function of time and as a function of pressure in respect of characteristics of the occlusion which corresponds respectively to a step-function reference signal and to a ramp-function reference signal.

Under these conditions FIG. 4 illustrates the curve representing the time-dependent variation in impedance $\Delta R$ which is recorded in respect to a step-function occlusion which is also shown in the same graph. If so required, preliminary resetting of this curve to zero may be carried out in order to eliminate the artefact resulting from inflation of the pneumatic garrot. As can be seen from this figure, the curve has a substantially linear initial phase corresponding to the filling of the veins in the non-distended state by means of the arterial and capillary system. The curve then assumes an exponential shape as soon as the elasticity of the walls of the veins comes into action and finally stabilizes when the pressure of these latter becomes equal to the applied counter-pressure. At the end of the sequence, the collar is deflated by means of the solenoid-actuated valve 8. The volume of blood stored in the veins is then discharged into the haemodynamic resistance located downstream of the occlusion. As illustrated in FIG. 4, the curve then has a falling exponential shape with a predetermined time constant.

The above-mentioned curve provides a measurement of the slope at the origin $P_R$, the maximum amplitude $\Delta R$ at the time of filling, the slope $P_V$ at the time of evacuation, the time constant $C_V$, and the maximum amplitude $A_V$ at the time of evacuation. All these values are representative of measurement indices in accordance with a given law. After suitable standardization, the measurement indices represent items of information parameters on the limb under examination and make it possible to establish a suitable diagnosis.

As a result of the occlusion thus achieved, filling of the capacities located upstream of the thigh-strap is in fact caused to take place within the superficial and deep veins without hindering the supply of arterial blood. This filling operation is first proportional to the arterial flow rate and takes place until equilibrium is attained between the occlusion pressure of the order of 50 mmHg, for example, and the venous pressure. The equilibrium results from that which exists between the arterial blood supply and the venous leakage which corresponds to the saturation phase, as illustrated by FIG. 4.

Suppression of the occlusion which is followed by an abrupt decrease in volume of the limb similarly corresponds to fast leakage of the venous blood. On the basis of the curve obtained (shown in FIG. 4), it is therefore possible to calculate certain other indices while taking into account the mean impedance R of the limb and the impedance variations $\Delta R$ which directly relate to variations in the venous volume as a function of time. Under these conditions, the slope at the origin $P_R$ represents the arterial blood-flow in the initial phase whilst the amplitude $A_R$ of filling characterizes the volume capacity of the veins. Similarly, the initial slope $P_V$ at the time of evacuation represents the evacuation rate and is consequently related to the resistance of the venous system at the time of evacuation. The time constant $C_V$ is a function both of the venous capacity and of the resistance at the time of evacuation. Finally, the amplitude $A_V$ of evacuation is related to the filling amplitude.

The device in accordance with the invention, compares the different noted indices which have thus been measured and suitably standardized with normal limb threshold values as predetermined by means of a preliminary statistical study of a healthy reference population. The reference indices measured on this healthy population thus define a statistical dispersion, that is to say a mean value, a standard deviation and two pathological thresholds. Subsequent comparison of the measured indices relating to the limb under examination with the reference threshold indices aforesaid makes it possible to determine a series of directly accessible elements of appreciation in the case of each index or in the case of a number of indices taken in suitable combinations.

Figure 5:
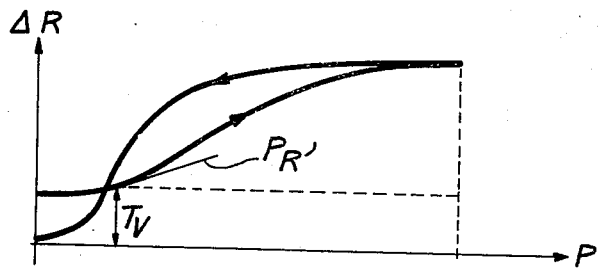

FIG. 5 illustrates another measurement curve in which the variation in limb impedance $\Delta R$ is no longer given as a function of time. Rather, it is given as a function of the variation in pressure applied to the limb. This curve corresponds to a ramp-function occlusion reference signal wherein the pressure applied to the limb increases in accordance with a linear law. In this particular case, the pressure on the collar 2 is applied slowly in order to remain in equilibrium with the pressure of the veins. The counter-pressure exerted and the value of the impedance are recorded simultaneously, as illustrated in FIG. 5, which initially exhibits a horizontal portion corresponding to the increasing pressure applied by the collar without variation in the venous volume. As soon as the counter-pressure has attained the pressure of the veins at the end of filling of these latter, a linear increase in volume then takes place as a function of the applied pressure. The curve of FIG. 5 shows that the limb then undergoes inflexion progressively as the veins become saturated as a result of a change in elasticity. Conversely, a return to zero pressure, which always takes place slowly, gives rise to a curve having a shape which is similar to that of pressurization but with a slight hysteresis effect.

Whether the occlusion reference signal controlling the pressure applied to the limb by the collar 2 is a step function, or a ramp function in accordance with either of the two solutions aforementioned or in accordance with any other suitable law, the measurement of characteristic indices on the recorded curves makes it possible to supply useful information for diagnosis. In the step-function test in particular, the measured indices give access to the dynamic characteristics of the venous system while the ramp-function test supplies information on the static characteristics of the venous system, especially in regard to the venous pressure $T_V$ (FIG. 5)

which expresses the filling in the state of rest while the slope of the initial linear portion $P_R$ represents the overall elasticity of the limb veins.

Figure 6:
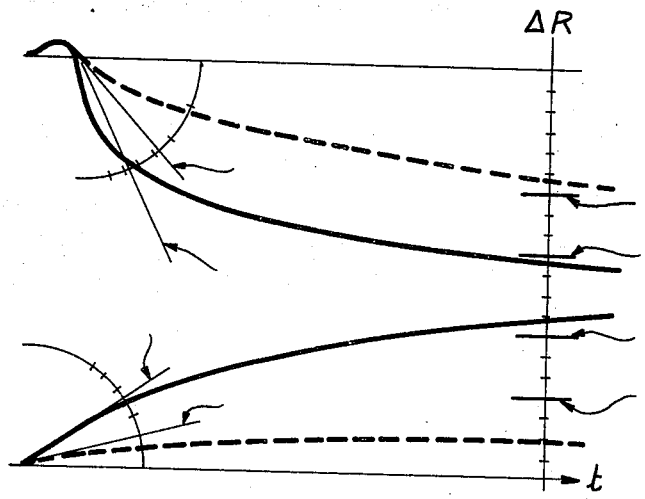
FIG. 6 is a schematic illustration showing the shape of the curves which can be recorded on an X/Y visual display device which is incorporated in the device according to the invention.

FIG. 6 shows the shape of the standardized curves which can be directly displayed by the recording and visual-display unit 23 of FIG. 3 in the case of a step-function occlusion reference signal. The curve of FIG. 4 is again shown in the diagram of FIG. 6, namely at the time of filling (bottom portion) and at the time of evacuation (top portion). The corresponding curves in dashed lines represent a pathological case situated outside the values of the threshold in the case of the slope at the point of origin and of the saturation level shown in this lines in the diagram. The full-line curves represent a normal case in the vicinity of the mean values which are also shown in thin lines in the same diagram. It is apparent from the diagram of FIG. 6 that, in the case of a direct reading, the apparatus is capable of supplying directly the measured values of the indices together with their comparison on the diagram itself with respect to the limits defining pathological behavior. Subsequent processing of these indices in accordance with suitable laws and criteria can then be carried out in the operator 28 in order to supply directly desired elements of appreciation which result in a final diagnosis.

Figure 7:
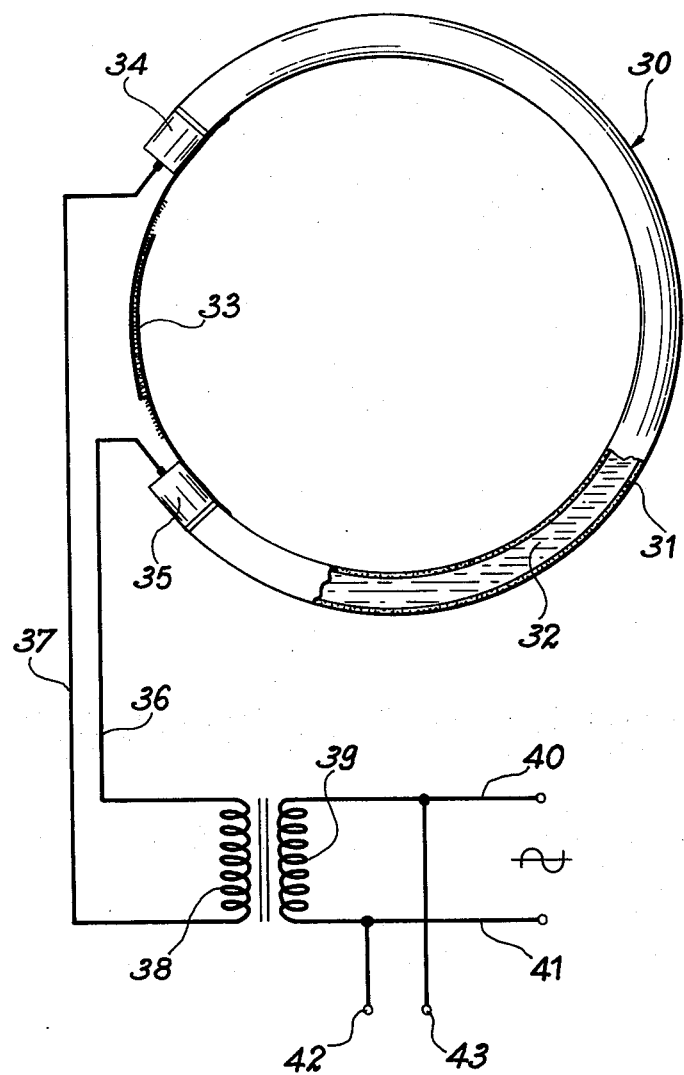
FIG. 7 illustrates an alternative embodiment of a plethysmograph which can be utilized in the device according to the invention.

FIG. 7 illustrates an alternative form of construction of a plethysmograph which can be employed in the device in accordance with the invention instead of the impedance plethysmograph which is illustrated in FIG. 2. In this alternative embodiment, the impedance supplied (or more precisely a variation in impedance) is no longer directly representative of the impedance of the actual limb under examination but consists of an impedance of an external device which is related to or associated with said limb and the measurement of which is also representative of the behavior of this latter. In particular, this alternative form of construction entails the use of a conventional extensometer gage constituted by a thin, flexible and extensible tube filled with mercury and connected to two electric wires which serve to connect the gage to a suitable current supply. If R is the electrical resistance of the gage thus formed, this latter can be expressed by the formula:

$$R = \rho l/s \tag{3}$$

where l and s represent respectively the length and the cross-sectional area of the mercury-filled tube, either by reason of the fact that the volume v of said tube remains constant $$R = \rho l^2/v \tag{4}$$

or by deriving $$dR = 2\rho l \, dl/v \tag{5}$$

showing that the variation in resistance is related to the elongation. If the tube of the gage is placed around a limb to be studied, it will permit a measurement of the variation in cross-section of this latter at the point at which it is located. The variation in resistance can be measured through an impedance-matching device constituted by a simple transformer. In order to ensure that the function relating dR and dl is made linear, it will only be necessary to divide the value of the signal by $\sqrt{R}$ by utilizing the same analog module or operator as in the case of the impedance plethysmograph shown in FIG. 2, the exponent n chosen in the case of formula (2) being equal to 0.5 ($dl = dR/K\sqrt{R}$), the sensitivity of the gage being constant in this case. The occlusion reference signal will be identical with the signal previously adopted while the characteristic indices and parameters also remain the same. As in the first alternative embodiment, a statistical study serves to determine the distribution of values of dl in the limbs of a healthy reference population by establishing in the same manner the pathological thresholds and the normal values in respect of the different parameters adopted.

In FIG. 7, the reference 30 designates the gage which is thus employed. The gage comprises an extensible tube 31 and an internal volume 32 of mercury, said tube being provided with means 33 for attaching the ends of this latter in order to surround the limb to be examined. Two contact electrodes 34 and 35 are provided at the extremities of the limb in order to ensure an electric connection with leads 36 and 37 which are connected to the secondary winding 38 of an impedance-matching transformer. The measuring current is supplied to the primary winding 39 of said transformer through leads 40 and 41 and the signal is collected at 42 and 43 at the terminals of said winding.

We claim:

1. A device for rheoplethysmography by occlusion adapted in particular to the study of vascular behavior of a lower limb of a patient comprising pressure-applying means for causing occlusion of a lower limb under study, means for controlling the characteristics of progressive variation in the pressure applied by the pressure-applying means as a function of time during occlusion of the limb under study, a plethysmograph for delivering signals which are representative of an electrical impedance related to said limb under study and of the variations in said electrical impedance, of a normal limb of the same type as the limb under study, and means for determining, from coefficients of standardization which are characteristic of the healthy vascular operation of a normal limb of the same type as the limb under study and said signals, indices which are representative of the vascular behavior of said limb under study, said pressure-applying means including a control loop having a amplifier for establishing a comparison between a predetermined reference value and the value of the pressure within the collar, a transducer for measuring said collar pressure, a circuit means for controlling the inflation of the collar, and a pump which inflates said collar.

2. A device according to claim 1, including means for the visual display of the standardized values of said indices.

3. A device according to claim 2, wherein the visual display means includes a calibrated galvanometer provided in the case of each index with references corresponding to predetermined pathological thresholds defining means for comparison with the predetermined thresholds.

4. A device according to claim 2, wherein the visual display means includes an X-Y recorder provided in the case of each index with references corresponding to predetermined pathological thresholds defining means for comparison with the predetermined thresholds.

5. A device according to claim 1 including means for comparing said indices with predetermined discrimination thresholds.

6. A device according to claim 1 wherein the pressure-applying means for causing occlusion of the limb includes a pneumatically inflated collar which surrounds said limb, and a pneumatic inflating device for inflating said collar.

7. A device according to claim 1, including means for releasing the occlusion in the form of a solenoid-actuated exhaust valve connected to said collar.

8. A device according to claim 1, wherein said measurement indices represent:

an index of rate of filling of the vascular territory during occlusion, characterized by an initial slope $P_r$ of a curve which gives the variation in measured limb impedance as a function of time, an index of extensibility at the time of limb filling, characterized by the amplitude of filling or the venous capacity $A_r$ as a function of the maximum value of the time-dependent variation in limb impedance, an index of rate of evacuation at release of the occlusion, characterized by a slope at a point of origin $P_v$ of a curve which represents the variation in limb impedance as a function of time, an evacuation index characterized by the amplitude of evacuation or the venous contraction $A_v$ as a function of the maximum value of the time-dependent variation in limb impedance, an evacuation time constant $C_v$ a coefficient of elasticity of the veins of the limb under study as a function of the variation in limb impedance in accordance with the applied pressure, a venous pressure defining a threshold from which a variation in limb impedance takes place as a function of the applied pressure.

9. A device according to claim 1, wherein the means for determining the indices from the coefficients of standardization and from the signals include an analog circuit and means for visually displaying and recording of curves of said signals.

10. A device according to claim 1 including a sequencer for programming the characteristics of the pressure applied by the pressure-applying means for programming the conditions of recording of the signals and for programming the measurement of the particular indices desired.

11. A device according to claim 10, wherein the pressure applied is represented by a step function, a ramp function, a ramp-step function, or the like.

12. A device according to claim 10 including a logical operator for assisting diagnosis the said operator comparing measured indices with predetermines values.

13. A device according to claim 1, wherein the plethysmograph includes a four-pole impedance plethysmograph.

14. A device according to claim 1, wherein the plethysmograph includes an extensometer gage.

* * * * *

UNITED STATES PATENT AND TRADEMARK OFFICE
CERTIFICATE OF CORRECTION

PATENT NO. : 4,169,463
DATED : October 2, 1979
INVENTOR(S) : Jean-Francois Piquard It is certified that error appears in the above-identified patent and that said Letters Patent are hereby corrected as shown below:

Column 1, line 57, after "of" insert --the--.
Column 2, line 10, after "examination" insert a comma.
Column 3, line 23, delete "the" first occurrence, and substitute therefor --an--;
         line 36, delete "corresponds" and substitute therefor --correspond--;
         line 47, delete "limb encircling" and substitute therefor --limb-encircling--;

Column 4, line 9, delete "fourpole" and substitute therefor --four-pole--;

line 17, before "power" insert --isolated--;
         line 58, after "abscissa" insert --generator--.
Column 5, line 29, delete "to" and substitute therefor --of--;
         line 55, delete "items of".

Signed and Sealed this

Twenty-sixth Day of February 1980

[SEAL]

Attest:

SIDNEY A. DIAMOND

Attesting Officer     Commissioner of Patents and Trademarks